US009089508B2

(12) United States Patent
Jackson et al.

(10) Patent No.: US 9,089,508 B2
(45) Date of Patent: Jul. 28, 2015

(54) METHOD OF TRANSFECTION AND COMPOSITIONS THEREFOR

(75) Inventors: David Charles Jackson, North Balwyn (AU); Weiguang Zeng, Kensington (AU); Brendon Yew Loong Chua, Heidelberg Heights (AU)

(73) Assignee: The University of Melbourne (AU)

( * ) Notice: Subject to any disclaimer, the term of this patent is extended or adjusted under 35 U.S.C. 154(b) by 295 days.

(21) Appl. No.: 12/682,415

(22) PCT Filed: Oct. 9, 2008

(86) PCT No.: PCT/AU2008/001501
§ 371 (c)(1),
(2), (4) Date: Aug. 17, 2010

(87) PCT Pub. No.: WO2009/046498
PCT Pub. Date: Apr. 16, 2009

(65) Prior Publication Data
US 2010/0310595 A1 Dec. 9, 2010

(30) Foreign Application Priority Data

Oct. 9, 2007 (AU) .............................. 2007905530
Oct. 9, 2007 (AU) .............................. 2007905536

(51) Int. Cl.
*A61K 39/00* (2006.01)
*C12N 15/87* (2006.01)
*C07K 1/107* (2006.01)

(52) U.S. Cl.
CPC .............. *A61K 39/00* (2013.01); *C07K 1/1075* (2013.01); *C12N 15/87* (2013.01); *A61K 2039/53* (2013.01); *A61K 2039/6018* (2013.01); *A61K 2039/622* (2013.01); *C12N 2810/855* (2013.01)

(58) Field of Classification Search
CPC ....... A61K 39/00; A61K 38/00; C12N 15/11; C12N 15/87
See application file for complete search history.

(56) References Cited

U.S. PATENT DOCUMENTS

| | | | |
|---|---|---|---|
| 2004/0191270 | A1 | 9/2004 | Drane et al. |
| 2008/0069831 | A1 | 3/2008 | Duke et al. |
| 2012/0064109 | A1 | 3/2012 | Jackson et al. |

FOREIGN PATENT DOCUMENTS

| | | | | |
|---|---|---|---|---|
| EP | 1 666 056 | | 6/2006 | |
| WO | WO-2004/014956 | | 2/2004 | |
| WO | WO-2004/014957 | | 2/2004 | |
| WO | WO2004014956 A1 * | | 2/2004 | ............. C07K 19/00 |
| WO | WO-2005/070959 | | 8/2005 | |
| WO | WO-2007/103322 A2 | | 9/2007 | |

OTHER PUBLICATIONS

Tam et. al. Synthesis and Applicantion of Peptide Dendrimers as Protein minmetics, Current Protocols in Protein Science, John Wiley and Sons, Inc. (1999) 18.5.1-18.5.35.*
Jackson, D.C. et al., "A totally synthetic vaccine of generic structure that targets Toll-like receptor 2 on dendritic cells and promoted antibody of cylotoxic T cell responses," PNAS, Oct. 26, 2004, vol. 101, No. 43, pp. 15440-15445.
International Search Report for corresponding International Patent Application No. PCT/AU2008/001501.
Amigorena S., "Fcγ Receptors and Cross-Presentation in Dendritic Cells," J. Exp. Med, vol. 195, pp. F1-F3 (Jan. 7, 2002).
Andra et al., "enhancement of endotoxin neutralization by coupling of a C12-alkyl chain to lactoferricin-derived peptide," Biochem J., Jan. 1, 2005, vol. 385., pp. 135-143.
Farley et al., "Lipopolysaccharide Structure determines Ionic and Hydrophobic binding of a cationic antimicrobial neutrophil granule protein," Infection and immunity, Jun. 1988, vol. 56(6), pp. 1589-1592.
Ismaili et al., "Monophosphoryl Lipid A activates both human dendritic cells and T cells," J. immunol, vol. 168, pp. 926-932 (2002).
Metzger et al., "Synthesis of Novel immunologically active tripalmitoyl-S-glycerylcysteinyl lipopeptides as useful intermediates for immunogen preparations," Int J. Peptide Protein Res., vol. 37, pp. 46-57 (1991).
Pina et al, "Shiga toxin B-subunit sequential binding to its natural receptor in lipid membranes," Biochimica et Biophysica Acta, 2007, vol. 1768, pp. 628-636.
Raffai et al., "Binding of an Antibody mimetic of the human low density lipoprotein receptor to apolipoprotein E is governed through electrostatic forces," The journal of Biological Chemisrty, vol. 275, pp. 7109-7116 (2000).
Raffai et al., "Molecular Characterization of two monoclonal antibodies specific for the LDL receptor-binding site of human apolipoprotein E," Journal of Lipid Research, vol. 36, pp. 1905-1918 (1995).
Office Action mailed on Jul. 3, 2012 for U.S. Appl. No. 13/268,069, filed Oct. 7, 2011 (7 pages).
Alphs, H. et al., "Protection against heterologous human papillomavirus challenge by a synthetic lipopeptide vaccine containing a broadly cross-neutralizing epitope of L2," Proceedings of the National Academy of Sciences of the United States of America, vol. 105, No. 15, pp. 5850-5855 (Apr. 15, 2008).
Baz, A. et al., "Branched and linear lipopeptide vaccines have different effects on primary CD4+ and CD8+ T-cell activation but induce similar tumor-protective memory CD8+ T-cell responses," Vaccine, vol. 26, No. 21, pp. 2570-2579 (May 19, 2008).

(Continued)

*Primary Examiner* — James H Alstrum Acevedo
*Assistant Examiner* — Jeanette Lieb
(74) *Attorney, Agent, or Firm* — Wilmer Cutler Pickering Hale and Door LLP

(57) ABSTRACT

The present invention relates to the targeted delivery of molecules to cells expressing toll-like receptors (TLRs). Aspects of the invention provide compounds comprising a positively charged group linked to a TLR ligand. These compounds are useful for in vitro and in vivo methods of transfection of TLR-expressing cells. Other aspects of the invention relate to the use of such compounds for repression of gene expression and DNA vaccination approaches.

23 Claims, 9 Drawing Sheets

(56) References Cited

OTHER PUBLICATIONS

Chua, B.Y. et al., "634 Enhancing Immunogenicity of HCV DNA Vaccines by Targeted Delivery to Dendritic Cells (DC)," Journal of Hepatology, Munksgaard International Publishers, vol. 48, pp. S236-S237 (Jan. 1, 2008).

Chua, B.Y. et al., "Dendritic cell acquisition of epitope cargo mediated by simple cationic peptide structures," Peptides, vol. 29, No. 9, pp. 881-890 (2008).

Chua, B.Y. et al., "Soluble proteins induce strong CD8+ T cell and antibody responses through electrostatic association with simple cationic or anionic lipopeptides that target TLR2," The Journal of Immunology, vol. 187, No. 4, pp. 1692-1701 (Jul. 8, 2011).

European Office Action issued by the European Patent Office for Application No. 08800135.9 mailed on Aug. 11, 2014 (7 pages).

Office Action issued by the United States Patent and Trademark Office for U.S. Appl. No. 13/268,069 mailed on Apr. 11, 2013 (11 pages).

Office Action issued by the United States Patent and Trademark Office for U.S. Appl. No. 13/268,069 mailed on Jul. 22, 2014 (23 pages).

Office Action issued by the United States Patent and Trademark Office for U.S. Appl. No. 13/268,069 mailed on Jul. 3, 2012 (10 pages).

Supplementary European Search Report and Written Opinion issued by the European Patent Office for Application No. EP08800135.9 mailed on Feb. 16, 2012 (12 pages).

Dikopoulos, N. et al., "Novel Peptide-based Vaccines Efficiently Prime Murine "Help"—Independent CD8+ T Cell Responses in the Liver," Hepatology, vol. 40, No. 2, pp. 300-309 (Aug. 1, 2004).

Futaki, S. et al., "Arginine-rich peptides: An abundant source of membrane-permeable peptides having potential as carriers for intracellular protein delivery," The Journal of Biological Chemistry, vol. 276, No. 8, pp. 5836-5840 (Nov. 17, 2000).

Gariepy, J. et al., "Vectorial delivery of macromolecules into cells using peptide-based vehicles," TRENDS in Biotechnology, vol. 19, No. 1, pp. 21-28 (Jan. 2001).

Gratton, J.-P. et al., "Cell-permeable peptides improve cellular uptake and theapeutic gene delivery of replication-deficient viruses in cells and in vivo," Nature Medicine, vol. 9, No. 3, pp. 357-362 (Mar. 1, 2003).

Gros, E. et al., "A non-covalent peptide-based strategy for protein and peptide nucleic acid transduction," Biochimica et Biophysica Acta, vol. 1758, No. 3, pp. 384-393 (2006).

Kawamura, K.S. et al., "Probing the Impact of Valency on the Routing of Arginine-rich Peptides into Eukaryotic Cells," Biochemistry, vol. 45, No. 4, pp. 1116-1127 (2006).

Lau, Y.F. et al., "Lipid-containing mimetics of natural triggers of innate immunity as CTL-inducing influenza vaccines," International Immunology, vol. 18, No. 2, pp. 1801-1813 (2006).

Riedl, P. et al., "Complexes of DNA vaccines with cationic, antigenic peptides are potent, polyvalent CD8(+) T-cell-stimulating immunogens," Methods in Molecular Medicine, Humana Press Inc., pp. 159-169, 17 pages (2006).

Riedl, P. et al., "Peptides containing antigenic and cationic domains have enhanced, multivalent immunogenicity when bound to DNA vaccines," Journal of Molecular Medicine, vol. 82, No. 2, pp. 144-152 (Feb. 1, 2004).

Schirmbeck, R. et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells," The Journal of Immunology, vol. 171, No. 10, pp. 5198-5207 (Nov. 15, 2003).

Tansey, W. et al., "Synthesis and characterization of branched poly(L-glutamic acid) as biodegradable drug carrier," Journal of Controlled Release, vol. 94, No. 1, pp. 39-51 (Jan. 8, 2004).

\* cited by examiner ved from" shall be taken to

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Cys-S2Pam2

<400> SEQUENCE: 2

Arg Arg Arg Arg Cys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Arg Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys-fluorescein or Lys-carboxylfluorescein

<400> SEQUENCE: 4

Arg Arg Arg Arg Lys
1               5

<210> SEQ ID NO 5
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg-fluorescein or Arg-carboxylfluorescein

<400> SEQUENCE: 5

Arg Arg Arg Arg
1
```

METHOD OF TRANSFECTION AND COMPOSITIONS THEREFOR This application is a U.S. National Phase application under 35 U.S.C. §371 of International Patent Application No. PCT/AU2008/001501 filed Oct. 9, 2008, which claims the benefit of Australian Patent Application No. 2007905530 filed Oct. 9, 2007 and Australian Patent Application No. 2007905536 filed Oct. 9, 2007, each of which is hereby incorporated by reference in its entirety.

SEQUENCE LISTING

The instant application contains a Sequence Listing which has been submitted via EFS-Web and is hereby incorporated by reference in its entirety. Said ASCII copy, created on Aug. 16, 2010, is named 22568120.txt and is 1,622 bytes in size.

FIELD OF THE INVENTION

The present invention relates generally to the field of cellular biology. More particularly, the present invention is directed to a method of transfecting cells, in particular dendritic cells, and to a method of eliciting an immune response. To this end, the present invention provides compounds comprising at least one positively charged group, capable of binding nucleic acids, linked to a moiety capable of interacting with one or more members of the toll-like receptor (TLR) family.

BACKGROUND TO THE INVENTION

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally-equivalent products, compositions and methods are clearly within the scope of the invention, as described herein.

All the references cited in this application are specifically incorporated by reference herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;

Reference to any prior art in this specification is not, and should not be taken as, an acknowledgment or any form of suggestion that this prior art forms part of the common general knowledge in Australia.

Delivery of molecules such as lipids, proteins, peptides, DNA, polysaccharides and/or combinations thereof (eg. lipopolysaccharides, lipoproteins), into cells is useful for a multitude of research and clinical purposes. For example, in order for researchers to study intracellular processes such as gene regulation and expression, DNA-protein interactions or protein-protein interactions, and so on, it is often essential to introduce molecules into cells, and desirable to do so with as high efficiency as possible. Currently researchers deliver molecules into cells, i.e. transfect cells, by a variety of means with variable efficiency. The efficiency of transfection of cells is dependent on a number of factors including cell type, rate and stage of cell division, and the individual properties of both the molecules to be transfected and the transfection reagent(s).

DNA vaccines are thought to elicit an immune response via uptake of DNA by antigen-presenting cells such as dendritic cells (DCs), which subsequently express the antigen encoded by the internalised DNA and present the antigen to the immune system as peptides in the context of MHC molecules. In small animal models, administration of DNA has been successful in inducing protective immune responses, but only low efficacies have been reported in human clinical trials, often requiring high doses of DNA to induce immune responses (Kutzler, M. A. & Weiner, D. B. 2004 J Clin Invest, 114(9), 1241-1244). Adenoviruses and retroviruses have been used as vectors for gene delivery, however concerns exist in relation to the safety of these vectors for human use (Buckley, R. H. 2002 Lancet, 360(9341), 1185-1186). To date, transfection of DCs with relatively safe, non-viral vectors has proven difficult.

DNA is a net negatively charged molecule. More specifically, the phosphate groups within the backbone of DNA are negatively charged. Therefore, cationic molecules, which have a net positive charge, can adsorb DNA via electrostatic interaction, and are potential carriers for DNA. Such cationic molecules include microparticles (Minigo, G. et al. 2007 Vaccine, 25(7), 1316-1327; Mollenkopf, H. J. et al. 2004 Vaccine, 22(21-22), 2690-2695), peptides (Gratton, J. P. et al. 2003 Nat Med, 9(3), 357-362; Riedl, P. et al. 2006 Methods Mol Med, 127, 159-169), or liposomes (Jiao, X. et al. 2003 Hepatology, 37(2), 452-460; Ewert, K. et al. 2002 J Med Chem, 45(23), 5023-5029).

Simply carrying DNA to antigen-presenting cells, however, is not sufficient enough to result in transfection, and in order to drive an antigen specific response, there must also be uptake of the DNA. Antigen-presenting cells of the immune system express toll-like receptors (TLRs) on their cell surface, which bind to a variety of ligands, largely derived from microorganisms. For example, TLR-2 is known to bind bacterial lipoproteins, TLR-4 is known to bind bacterial lipopolysaccharides, TLR-6, in association with TLR-1, is known to bind diacylated bacterial lipids, and TLR-9 binds to CpG DNA. Dendritic cell subsets have been shown to express no fewer than nine such TLRs. Engagement of one or more TLRs on the surface of DCs induces cell signalling pathways, which can lead to the maturation and activation of DCs, which is required for the induction of protective immunity.

The lipid moiety, dipalmitoyl-S-glyceryl cysteine (Pam$_2$Cys), is a synthetic analogue of a bacterial lipoprotein known as MALP-2, derived from the cytoplasmic membrane of *Mycoplasma fermentans*. Pam$_2$Cys is a ligand for both TLR-2 and TLR-6 (Okusawa, T. et al., *Infect Immun* 2004, 72(3), 1657-1665). Vaccines comprising Pam$_2$Cys coupled to peptide epitopes can induce strong humoral and cellular responses. Engagement of TLR-2 by Pam$_2$Cys coupled to peptide epitopes results in DC maturation, activation of transcription factors such as NF-κB, secretion of pro-inflammatory cytokines and eventual migration of DCs to the draining lymph nodes to activate epitope-specific naïve T cells (Jackson, D. C. et al. 2004 Proc Natl Acad Sci USA, 101(43), 15440-15445; Zeng, W. et al. 2002 J Immunol, 169(9), 4905-4912; Chua, B. Y. et al. 2007 Vaccine, 25(1), 92-101).

SUMMARY OF THE INVENTION

In work leading up to the present invention, the inventors sought to produce an efficient means of transfecting cells with nucleic acids. It was also sought to produce a DNA vaccine candidate targeting antigen-presenting cells, in particular dendritic cells, to elicit both humoral and cellular immune responses in a subject.

In a first aspect the present invention provides a compound comprising a positively charged group linked to at least one TLR ligand.

In a second aspect the present invention provides a complex comprising nucleic acid and a compound comprising a positively charged group linked to at least one TLR ligand, wherein the nucleic acid is associated with the compound by electrostatic interaction between the nucleic acid and the positively charged group.

In a third aspect the present invention provides a method of transfection comprising contacting a cell expressing a TLR with a complex comprising nucleic acid and a compound comprising a positively charged group linked to at least one TLR ligand, wherein the nucleic acid is associated with the compound by electrostatic interaction between the nucleic acid and the positively charged group.

In a fourth aspect the present invention provides a method of raising an immune response against an antigen, comprising administering to a subject a complex comprising nucleic acid and a compound comprising a positively charged group linked to at least one TLR ligand, wherein the nucleic acid is associated with the compound by electrostatic interaction between the nucleic acid and the positively charged group, and wherein the nucleic acid encodes the antigen or an epitope thereof.

In a fifth aspect the present invention provides a method of raising an immune response against an antigen, comprising administering to a subject cells transfected with a complex comprising nucleic acid and a compound comprising a positively charged group linked to at least one TLR ligand, wherein the nucleic acid is associated with the compound by electrostatic interaction between the nucleic acid and the positively charged group, and wherein the nucleic acid encodes the antigen or an epitope thereof.

In a sixth aspect the present invention also provides a method of repressing expression of a gene in a cell expressing a TLR, comprising administering to a subject a complex comprising nucleic acid and a compound comprising a positively charged group linked to at least one TLR ligand, wherein the nucleic acid is associated with the compound by electrostatic interaction between the nucleic acid and the positively charged group, wherein the nucleic acid is selected from the group consisting of: siRNA; shRNA; DNA encoding siRNA; and DNA encoding shRNA; and is targeted against the gene.

Further provided are uses of a compound comprising a positively charged group linked to at least one TLR ligand in: the manufacture of a vaccine for the induction of an immune response in a subject; the manufacture of a medicament for the treatment of a subject with a genetic abnormality or deficiency; the manufacture of a medicament for the treatment of a subject suffering from aberrant or otherwise unwanted expression of a gene; and in the manufacture of a reagent for the transfection of cells.

DETAILED DESCRIPTION OF THE INVENTION

Figure 1:
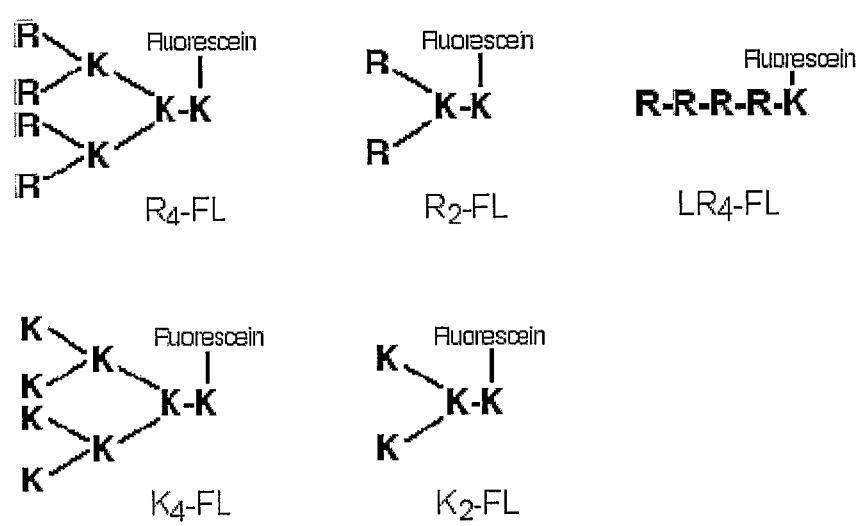
FIG. 1 is a diagrammatic representation of the various synthesized fluorescenated peptide constructs. Abbreviations; R, arginine; K, lysine; L, linear; FL, fluorescein or carboxylfluoresein.

Surprisingly, the inventors have found that the compounds of the present invention form a stable complex with DNA. DNA binds to the cationic portion of the compound and this complex is targeted, via the TLR ligand portion of the compound, to cells expressing receptors recognising the ligand, e.g. antigen-presenting cells such as DCs.

One advantage provided by the compounds of the present invention is that they are capable of targeting TLR-expressing cells. As the result of binding to TLRs, compounds of the present invention are internalised and also induce TLR-mediated signalling pathways. In particular embodiments, binding of TLR-2 by the $Pam_2Cys$ portion of the compounds of the present invention, causes DC maturation, resulting in migration of DCs to lymph nodes and efficient antigen presentation to T lymphocytes.

In a first aspect the present invention provides a compound comprising a positively charged group linked to at least one TLR ligand. In some embodiments the compounds of the present invention comprise a positively charged group covalently linked to at least one TLR ligand.

In a second aspect the present invention provides a complex comprising nucleic acid and a compound comprising a positively charged group linked to at least one TLR ligand, wherein the nucleic acid is associated with the compound by electrostatic interaction between the nucleic acid and the positively charged group.

In a third aspect the present invention provides a method of transfection comprising contacting a cell expressing a TLR with a complex comprising nucleic acid and a compound comprising a positively charged group linked to at least one TLR ligand, wherein the nucleic acid is associated with the compound by electrostatic interaction between the nucleic acid and the positively charged group.

In a fourth aspect the present invention provides a method of raising an immune response against an antigen, comprising administering to a subject a complex comprising nucleic acid and a compound comprising a positively charged group linked to at least one TLR ligand, wherein the nucleic acid is associated with the compound by electrostatic interaction between the nucleic acid and the positively charged group, and wherein the nucleic acid encodes the antigen or an epitope thereof.

In a fifth aspect the present invention provides a method of raising an immune response against an antigen, comprising administering to a subject cells transfected with a complex comprising nucleic acid and a compound comprising a positively charged group linked to at least one TLR ligand, wherein the nucleic acid is associated with the compound by electrostatic interaction between the nucleic acid and the positively charged group, and wherein the nucleic acid encodes the antigen or an epitope thereof.

In a sixth aspect the present invention also provides a method of repressing expression of a gene in a cell expressing a TLR, comprising administering to a subject a complex comprising nucleic acid and a compound comprising a positively charged group linked to at least one TLR ligand, wherein the nucleic acid is associated with the compound by electrostatic interaction between the nucleic acid and the positively charged group, wherein the nucleic acid is selected from the group consisting of: siRNA; shRNA; DNA encoding siRNA; and DNA encoding shRNA; and is targeted against the gene.

In additional aspects the present invention also provides uses of a compound comprising a positively charged group linked to at least one TLR ligand in: the manufacture of a vaccine for the induction of an immune response in a subject; the manufacture of a medicament for the treatment of a subject with a genetic abnormality or deficiency; the manufacture of a medicament for the treatment of a subject suffering from aberrant or otherwise unwanted expression of a gene; and in the manufacture of a reagent for the transfection of cells.

The present invention provides compounds comprising a positively charged group linked to a TLR ligand, i.e. a moiety that binds to a cell surface TLR. Binding of the TLR ligand to the TLR results in uptake of the compound by a cell expressing the TLR, and/or signalling via the TLR-mediated signalling pathway.

The term "TLR" as used herein means refers to one or more toll-like receptors, which can be defined as a class of membrane-bound receptors that bind to structurally conserved molecules derived from microbes. Thirteen TLRs, TLR-1 to TLR-13, have thus far been identified, and it is estimated that most mammalian species have between ten and fifteen types of Toll-like receptors. (Du, X. et al 2000. Eur. Cytokine Netw. 11:362-371; Chuang, T. H., and Ulevitch, R. J. 2000. Eur. Cytokine Netw. 11:372-378; Tabeta, K. et al 2004 Proc. Natl. Acad. Sci. USA 101:3516-3521). TLRs are a type of pattern recognition receptor (PRR) and their ligands are known collectively as pathogen-associated molecular patterns (PAMPs).

A "TLR ligand" as used herein means a molecule that selectively or preferentially binds to a TLR. Examples of TLR ligands include conserved features in pathogens and include: bacterial cell-surface lipopolysaccharides (LPS), lipoproteins, lipopeptides and lipoarabinomannan; proteins such as flagellin from bacterial flagella; double-stranded RNA of viruses or the unmethylated CpG motifs of bacterial and viral DNA; and certain other RNA and DNA. Endogenous ligands of TLRs have also been identified, including fibrinogen, heat shock proteins (HSPs), and DNA.

Table 1 lists TLRs, presently known to be expressed on dendritic cells, together with their corresponding ligands.

Pam$_2$Cys has the structure of Formula (I):

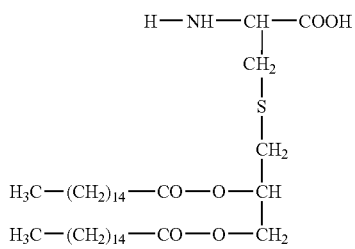

Other lipid moieties which may be used to target cell surface TLRs include palmitoyl, myristoyl, stearoyl, lauroyl, octanoyl, or decanoyl. Preferred groups include Pam$_2$Cys, Pam$_3$Cys, Ste$_2$Cys, Lau$_2$Cys, and Oct$_2$Cys.

Positively charged groups of the present invention include but are not limited to the cationic compounds listed in Table 2 and the polycationic compounds described in U.S. Pat. No. 6,689,478 and U.S. Pat. No. 4,035,558.

TABLE 1

Toll-like receptors expressed by DC

| Family | Receptor | Ligand | References |
|---|---|---|---|
| Toll-like receptors | TLR-1 | triacylated bacterial lipids (TLR-1 & 2) | (Takeuchi 2002) |
| | TLR-2 | peptidoglycan, yeast zymosan, bacterial lipoproteins | (Schwandner 1999, Ozinsky 2000, Takeuchi 2000, Schjetne 2003) |
| | TLR-3 | double stranded RNA | (Alexopoulou 2001) |
| | TLR-4 | LPS, hsp60 & hsp70 | (Poltorak 1998, Chow 1999, Asea 2002, Bulut 2002, Husebye 2006) |
| | TLR-5 | flagellin | (Hayashi 2001) |
| | TLR-6 | diacylated bacterial lipids (TLR-2 & 6) | (Morr 2002, Okusawa 2004) |
| | TLR-7 | imidazoquinoline compounds | (Hemmi 2002) |
| | TLR-8 | single stranded RNA | (Heil 2004) |
| | TLR-9 | CpG DNA | (Hemmi 2000, Takeshita 2001) |
| | TLR-10 | yet to be discovered | (Flacher 2006) |
| | TLR-11 | yet to be discovered | (Pepper 2008) |

Abbreviations:
CpG, cytosine phosphate guanine;
hsp, heat shock protein;
LPS, lipopolysaccharide;
RNA, ribonucleic acid An exemplary compound of the present invention is a cationic peptide linked to the lipopeptide "Pam$_2$Cys". One of skill in the art would understand that the term "lipopeptide" means any composition of matter comprising one or more lipid moieties and one or more amino acid sequences that are conjugated. "Pam$_2$Cys" (also known as dipalmitoyl-S-glyceryl-cysteine or S-[2,3bis(palmitoyloxy) propyl]cysteine has been synthesised (Metzger, J. W. et al. 1995. J Pept Sci 1: 184) and corresponds to the lipid moiety of MALP-2, a macrophage-activating lipopeptide isolated from *Mycoplasma fermentans* (Sacht, G. et al. 1998. Eur J Immunol 28:4207; Muhiradt, P. F. et al. 1998. Infect Immun 66: 4804; Muhiradt, P. F. et al. 1997. J Exp Med 185: 1951). Pam$_2$Cys is known to be a ligand of TLR-2.

TABLE 2

Cationic compounds

| Cationic Compounds | References |
|---|---|
| Penetratin | (Christiaens 2004) |
| HIV Tat 48-60 | (Fawell 1994) |
| HIV Rev 34-50 | (Futaki 2001) |
| Transportan | (Pooga 1998) |
| Oligoarginine peptides (linear and branched) | (Buschle 1997, Mitchell 2000) |
| Oligolysine peptides (linear and branched) | |
| Pyrrrochoricin | (Otvos 2004) |
| Alpha-helical amphipathic model peptide | (Oehlke 1998) |
| Polylysine | (Wagner 1990) |

TABLE 2-continued

Cationic compounds

| Cationic Compounds | References |
|---|---|
| Protamine (e.g. salmon protamine) | (Wagner 1990) |
| FL17 ($[(Me_2NCH_2CHOHCH_2)_n]^{n+}Cl_n$) | (Billingham 1997) |
| Magnafloc 1697 | (Billingham 1997) |
| ($[(CH_2CHCH_2N(Me)_2CH_2CHCH_2)_n]^{n+}Cl_n$) | |

Since nucleic acids, due to the phosphate groups within the backbone of nucleic acids, are net negatively charged molecules, they are bound by the positively charged groups of the compounds of the present invention, via electrostatic interaction, to form a stable complex.

In one embodiment, the positively charge group is a linear or branched peptide comprising arginine or lysine residues.

Reference to a "nucleic acid" should be understood as a reference to both deoxyribonucleic acid (DNA) and ribonucleic acid (RNA), including double-stranded DNA, double-stranded RNA, single-stranded DNA, single-stranded RNA, small interfering RNA molecules (siRNA), triplexes, quadruplexes and any multi-stranded (multiplex) nucleic acid molecule, nucleic acid hybrids such as peptide nucleic acids (PNA), a molecule comprising both deoxyribonucleic acid bases and ribonucleic acid bases, and any nucleotide variant.

In one embodiment, nucleic acid molecules are provided as "plasmids". Reference to "plasmids" should be understood as a reference to a nucleic acid molecule which is transmissible to a host cell and may undergo replication in the host cell. The nucleic acid molecule should not however, be limited to plasmids, but may be any nucleic acid molecule, including viral DNA or RNA.

One of skill in the art would appreciate that transfecting cells with nucleic acids is useful for many research and clinical applications. Reference to "transfection" should be understood as reference to a process by which exogenous molecules, including nucleic acids, are introduced into cells.

Many research applications require transfection of cells. Currently researchers introduce molecules into cells, i.e. transfect cells, by a variety of means with variable efficiency. Several transfection reagents are currently available to the researcher, including FUGENE. However, the efficiency of transfection of cells is dependent on, for example, cell type, rate and stage of cell division, and the individual properties of both the molecules to be transfected and the transfection reagent(s).

The compounds of the present invention are particularly useful for transfection of cells expressing TLRs. Therefore, cells either naturally expressing TLRs or cells that have been stably transfected to express a TLR, whether it be the entire receptor or a modified receptor lacking the intracellular signalling domain, can be transfected with nucleic acids complexed with the compounds of the present invention.

A "cell" should be understood as any cell into which the nucleic acid molecule is delivered by the compounds of the present invention. The cell may be an in vitro, in vivo or ex vivo cell. The cell may be isolated or form a part of the organs or tissues of a living animal. A cell may also be a microorganism such as bacteria, yeast, fungi, moulds, parasites, algae and so on. A cell can also be a cultured animal cell or cell line, or an artificial cell.

Reference to "isolated", in terms of the cells of certain embodiments of the present invention, should be understood as a reference to material that is removed from its original environment (e.g., the natural environment if it is naturally occurring). For example, a cell present in the tissue of a living organism is not isolated, but the same cell, when separated from some or all of the co-existing cells in the natural system, is isolated.

One aspect of the present invention provides compounds comprising a positively charged group, linked to a TLR ligand, which can form a stable complex with nucleic acids via electrostatic interaction between the positively charged group and the negatively charged nucleic acid. The compounds of the present invention provide a means of targeting nucleic acid to cells expressing TLR.

In one embodiment, the present invention provides compounds comprising a cationic peptide, linked to a TLR ligand, which can form a stable complex with DNA via electrostatic interaction between the cationic peptide and the negatively charged DNA. Such compounds provide a means of targeting DNA to cells expressing TLRs, e.g. antigen-presenting cells, and more particularly DCs.

In another embodiment, the invention provides a method of transfection comprising contacting a cell expressing a TLR with a complex comprising nucleic acid and a compound comprising a positively charged group linked to at least one moiety that binds to a TLR, wherein the nucleic acid is associated with the compound by electrostatic interaction between the nucleic acid and the positively charged group.

In a further embodiment, the present invention provides a method of raising an immune response against an antigen, comprising administering to a subject a complex comprising nucleic acid and a compound comprising a positively charged group linked to at least one moiety that binds to a TLR, wherein the nucleic acid is associated with the compound by electrostatic interaction between the nucleic acid and the positively charged group, and wherein the nucleic acid encodes the antigen or an epitope thereof.

In yet another aspect, the present invention provides a method of raising an immune response against an antigen, comprising administering to a subject cells transfected with a complex comprising nucleic acid and a compound comprising a positively charged group linked to at least one moiety that binds to a TLR, wherein the nucleic acid is associated with the compound by electrostatic interaction between the nucleic acid and the positively charged group, and wherein the nucleic acid encodes the antigen or an epitope thereof.

Contacting DCs with compounds of the present invention can result in the maturation or activation of DCs, as indicated by an increase in cell surface MHC Class II expression. Therefore, compounds comprising a TLR ligand can be useful not only for targeting DCs but also for their activation via TLRs and downstream signalling molecules such as MyD88.

Consequently, the compounds of the present invention are useful for activating DCs. In order for dendritic cells to induce an immune response, they must first be activated such that they express the necessary adhesion and co-stimulatory molecules to migrate to lymph nodes and activate T lymphocytes. Compounds comprising TLR ligands complexed with DNA are particularly useful for activating DCs, and when the DNA encodes a protein, the transfected DCs present peptide fragments of the translated DNA-encoded protein to immune cells, thereby invoking a cellular and humoral immune response. In other words, the compounds of particular embodiments of the present invention when complexed to DNA, are useful for DNA vaccination approaches.

Reference to "DNA vaccination" as used herein means reference to administration of DNA to a subject in order to induce an immune response to the protein encoded thereby. The compounds of the present invention may be administered directly to a subject by any route, including but not limited to: intravenous; intranasal; intramuscular; oral; rectal and so on.

Reference to "immune response" as used herein means a reference to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Reference to "T lymphocyte response" as used herein means a reference to the component of the immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

In addition to their use in DNA vaccination, the compounds of the present invention are useful for a number of other clinical applications. For example, treatments for autoimmune disease or cancer may require transfection of autologous cells, such as hemopoietic stem cells (HSCs) or peripheral blood mononuclear cells (PBMCs). Such cells can be harvested from a subject, cultured in vitro, optionally differentiated into DCs by methods well known in the art, and/or transfected with nucleic acid, and subsequently infused back into the subject. In some embodiments, the nucleic acid encodes a vaccine antigen and the transfected cells may be intended to invoke an immune response. In other embodiments, the nucleic acid may encode a cytokine or an antigenic tolerogen.

In another aspect, the present invention provides a method of repressing expression of a gene in a cell expressing a TLR, comprising administering to a subject a complex comprising nucleic acid and a compound comprising a positively charged group linked to a TLR ligand, wherein the nucleic acid is associated with the compound by electrostatic interaction between the nucleic acid and the positively charged group, and wherein the nucleic acid is selected from the group consisting of: siRNA; shRNA; DNA encoding siRNA; and DNA encoding shRNA; and wherein the siRNA or shRNA is targeted against the gene.

"Treating" or "treatment" includes the administration of the compositions, compounds or agents of the present invention to prevent or delay the onset of the symptoms, complications, or biochemical indicia of a disease, alleviating or ameliorating the symptoms or arresting or inhibiting further development of the disease, condition, or disorder (e.g., an infectious disease, inflammation, or an autoimmune disease). "Treating" further refers to any indicia of success in the treatment or amelioration or prevention of the disease, condition, or disorder (e.g., an infectious disease, inflammation, or an autoimmune disease), including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with an infectious disease, inflammation, or an autoimmune disease. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of an infectious disease, inflammation, or an autoimmune disease but does not yet experience or exhibit symptoms, inhibiting the symptoms of an infectious disease, inflammation, or an autoimmune disease (slowing or arresting its development), providing relief from the symptoms or side-effects an infectious disease, inflammation, or an autoimmune disease (including palliative treatment), and relieving the symptoms of an infectious disease, inflammation, or an autoimmune disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

In additional aspects the present invention provides uses of compounds comprising a positively charged group linked to a TLR ligand in: the manufacture of a vaccine for the induction of an immune response in a subject; the manufacture of a medicament for the treatment of a subject with a genetic abnormality or deficiency; the manufacture of a medicament for the treatment of a subject suffering from aberrant or otherwise unwanted expression of a gene; and in the manufacture of a reagent for the transfection of cells.

The compounds and the methods set forth herein can be used for both medical applications and veterinary applications. Typically, the product is used in humans, but may also be used in other mammals. The terms "patient" and "subject" are intended to denote a mammalian individual, and are so used throughout the specification and in the claims. The primary applications of the invention involve human patients or subjects, but the invention may be applied to laboratory, farm, zoo, wildlife, pet or sport animals.

It would be appreciated that the person of skill in the art may introduce any combination of positively charged group and TLR ligand as befits the desired application.

The present invention will now be described further with reference to the following non-limiting examples:

Example 1

Synthesis of Cationic Peptides

Branched peptide constructs were synthesized by using lysine residues to provide the branching points of a scaffold template. Depending on the number of branch points present in the scaffold, di or tetra cationic structures were produced (FIG. 1). These branched constructs were synthesised on PEG-S RAM resin (Rapp Polymere, Tübingen, Germany; substitution factor 0.27 mmol/g). Fmoc-lysine(Mtt)-OH (Novabiochem, Läufelfingen, Switzerland) was first coupled to the resin in 4-fold excess with equimolar amounts of O-benzotriazole-N,N,N,N',N'-tetamethyl-uronium-hexafluorophosphate (HBTU; Novabiochem, Darmstadt, Germany), 1-hydroxybenzotriazole (HOBt) and a 1.5-fold molar excess of diisopropylethylamine (DIPEA; Sigma, Castle Hill, Australia). Acylation was carried out for 40 minutes and complete reaction was confirmed by the trinitrobenzylsulfonic acid (TNBSA) test (21). Removal of the Fmoc protective group on the α-amino group was achieved with 2.5% diazabicyclo[5.4.0]undec-7-ene (Sigma, Steinheim, Germany) and Fmoc-lysine (Fmoc)-OH (Auspep, Melbourne, Australia) coupled such that following removal of the Fmoc groups, two primary amino groups were exposed to act as branching points. Dimethylformamide (DMF; Auspep, Melbourne, Australia) was used to wash the resin between each acylation and deprotection step. Subsequent amino acids were coupled at a 4-fold excess and acylation carried out for 60 minutes. For the assembly of tetravalent constructs, an additional round of acylation was performed for 60 minutes using Fmoc-lysine(Fmoc)-OH to produce four branch points. To enable chemoselective ligation of a group containing an amino acid to a tetravalent arginine construct (R4), cysteine was inserted at the C-terminus of the construct to yield R4-Cys. For carboxyfluorescein conjugation onto branched peptide constructs, N-terminal Fmoc groups were not removed following the last acylation reaction. Instead, the Mtt protective group present on the ε-amino group of the C-terminal lysine was removed by treatment with 1% TFA in dichloromethane (Ajax Finechem, Seven Hills, Australia). 5(6)-carboxyfluorescein (Fluka BioChemika, Switzerland) was then coupled to the exposed ε-amino group using a 4-fold excess in the presence of equimolar amounts of HOBt, HBTU and a 1.5 fold molar excess of DIPEA for 18 hours in the dark. Following acylation, the resin was washed with DMF and N-terminal Fmoc groups were removed. All peptides were cleaved from the solid phase support and side chain protecting groups simultaneously. The purity of peptides was assessed by reverse phase analytical chromatography using a Vydac C4 column (4.6 mm×250 mm) or a C8 column (4.6 mm×250 mm) installed in a Waters 3 HPLC chromatography system. A flow rate of 1 ml/min using 0.1% TFA in H2O and 0.1% TFA in acetonitrile as the limit solvent was used to develop chromatograms. Where necessary, peptides were purified using a semi-preparative Waters or GBC HPLC system and a semipreparative Vydac C4 column (10 mm×300 mm) at a flow rate of 2.5 ml/min. Estimation of peptide content was determined by UV spectrophotometry where the absorbance of fluorescenated peptides was determined at 496 nm and concentration calculated using a molar extinction coefficient of 83,000 $M^{-1}$ $cm^{-1}$. Schematics of the synthesised fluorescenated branched peptide constructs are shown in FIG. 1.

For lipidation of peptides, lipid moieties were assembled by coupling N-fluorenylmethoxycarbonyl-S-(2,3-dihydroxypropyl)-cysteine (Fmoc-Dhc-OH) at a 4-fold excess in the presence of equivalent amounts of HOBt and DICI in 50% DCM in DMF onto the ε-amino group of the C-terminal lysine. Acylation was carried out for 40 minutes and was repeated until successful coupling was confirmed using the trinitrobenezene sulfonic acid test. Lipidation of the two hydroxy groups of the resin-bound Fmoc-Dhc-peptide was carried out overnight using a solution containing an equimolar amount of DMAP, a 10-fold excess of fatty acid and a 12-fold excess of DICI.

Example 2

Retardation of DNA migration by $R_4$

Figure 2:
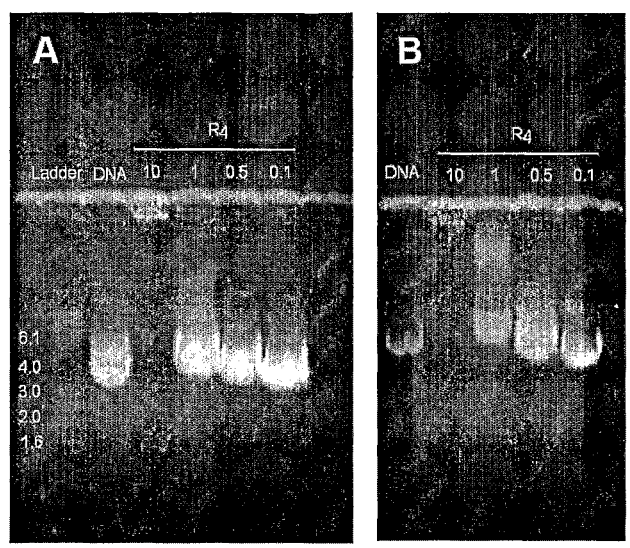
FIG. 2 is a photographic representation of an agarose gel analysis of R$_4$ and DNA interactions. Varying amounts (10, 1, 0.5 or 0.1 μg) of R$_4$ were incubated with 1 μg of either (A) pEGFP-N1 plasmid or (B) pCI-HA plasmid for 30 mins at 37° C. Samples were then ran on a 1% agarose gel containing SYBR-Safe DNA gel stain so that DNA could be visualised under UV light.

To investigate the association between the branched peptide $R_4$ and DNA, a constant amount of DNA plasmid pEGFP-N1 or pCI-HA, which encode for green fluorescent protein and influenza HA protein respectively, were incubated with varying amounts of $R_4$ and analysed by agarose gel electrophoresis (FIG. 2).

By increasing the amount of $R_4$ in each sample, DNA migration could be affected. Partial retardation of DNA plasmid migration towards the anode, as visualised by ethidium bromide fluorescence, was evident when 0.1-0.5 μg of $R_4$ was used whereas DNA samples incubated with higher amounts of $R_4$ moved at a slower rate. Total retardation of DNA migration was achieved when 10 μg of $R_4$ was present as evidenced by the appearance of a band of DNA at the origin. This band, however, appeared quite faint suggesting that there was little DNA in this sample. This may be due to: $R_4$ inhibiting the binding of ethidium bromide to the DNA; and/or the interaction between $R_4$ and DNA results in the formation of an insoluble complex that diffuses into the electrophoresis buffer rather than migrating through the agarose gel. These results suggest that the positively charged amino and guanidine groups of $R_4$ are able to neutralise the negatively charged phosphate groups within the DNA backbone to retard its ability to migrate towards the anode.

Example 3

Formation of $R_4$-DNA Complexes

Figure 3:
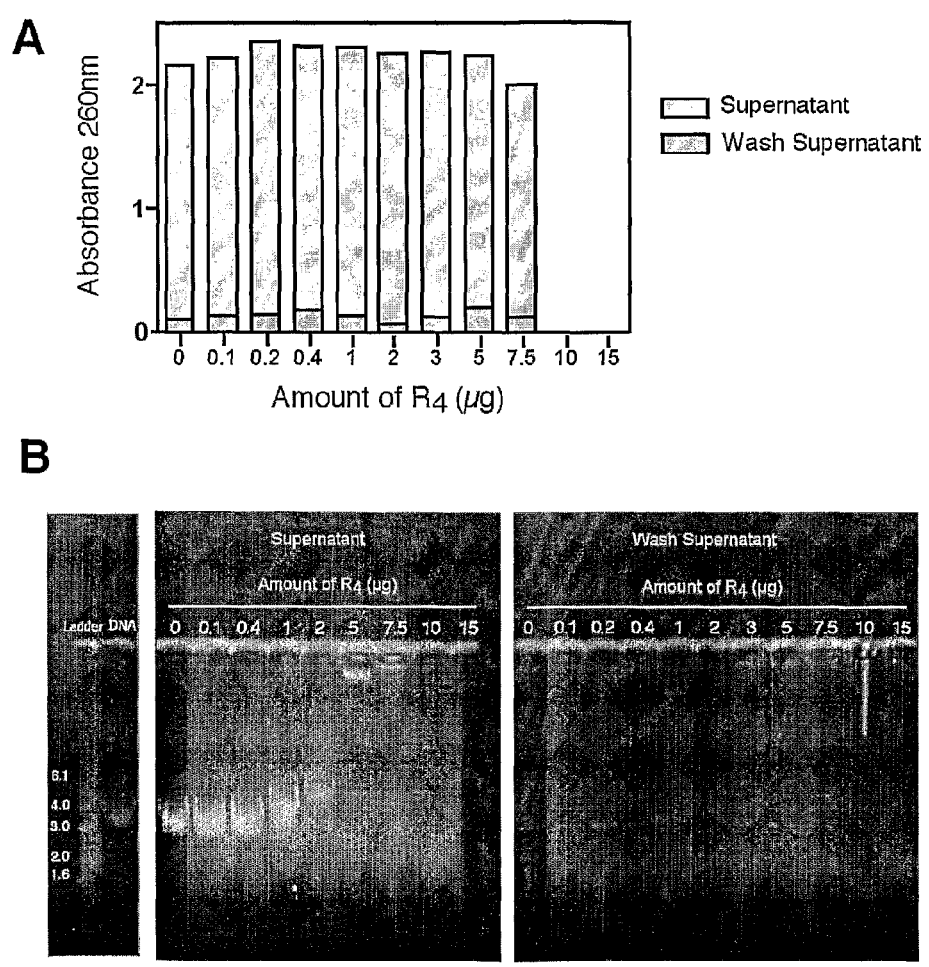
FIG. 3 shows absorbance readings at 260 nm of solutions containing R$_4$ and DNA. Increasing amounts of R$_4$ were incubated with 10 g of pCI-HA plasmid for 30 mins at 37° C. in a total volume of 100 μl of water. (A) Samples were centrifuged at 9300 g to pellet any insoluble complexes and absorbance readings of the collected supernatants were measured at 260 nm (light grey bars). Absorbance readings of wash supernatants after pelleted samples were resuspended with 100 μl of water were also measured (dark grey bars). (B) Supernatants and wash supernatants were also run on a 1% agarose gel containing SYBR-Safe DNA gel stain to detect the presence of DNA in these samples.

In order to confirm the binding of $R_4$ to DNA, the amount of DNA in the supernatant of centrifuged mixtures containing increasing amounts of $R_4$ and DNA was determined by measuring the absorbance at 260 nm (FIG. 3A). The ability of $R_4$ to precipitate DNA out of solution by neutralisation of its charge would result in less DNA in the solution and would therefore indicate an association between the two. It was found that the amount of DNA in the centrifuged supernatant did not vary dramatically when incubated with 0.1 μg to 5 μg of $R_4$. A slight decrease, however, resulted when 7.5 μg of $R_4$ was used and no DNA was detected in solutions containing more than this amount. This result indicates that the amount of $R_4$ present is proportional to the precipitation of DNA out of solution. Absorbance readings were also taken on the wash supernatant used to resuspend any centrifuged insoluble material. The presence of little DNA in these samples suggests that the $R_4$-DNA precipitates are stable and that DNA is unlikely to dissociate from this complex.

Agarose gel analysis (FIG. 3B) demonstrates that DNA bands were evident in supernatant samples containing 0.1-7.5 μg of $R_4$ but not in samples containing 10 or 15 μg of $R_4$. Retardation of DNA migration is also evident in samples containing 1 μg or more of $R_4$.

Example 4

Transfection of DCs with $R_4(S_2Pam_2Cys)$-DNA

Figure 4:
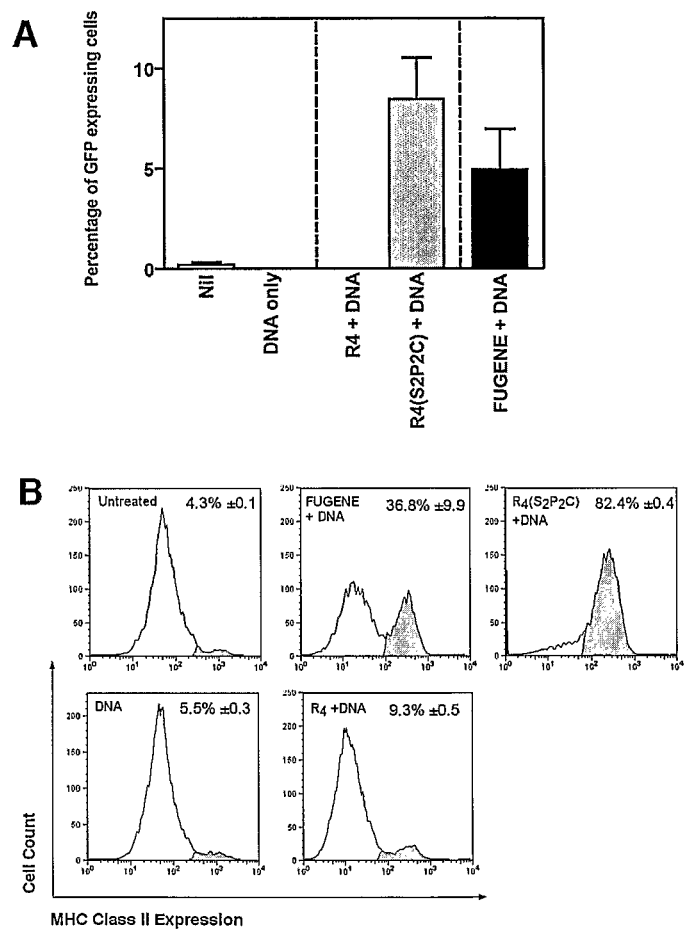
FIG. 4 is a graphical representation of the transfection of D1 cells with pEGFP-N1 plasmid and upregulation of MHC Class II expression on D1 cells. D1 cells (4×10$^5$), derived from BALB/c splenocytes, were cultured at 37° C. in an atmosphere of 5% CO$_2$ with 1 μg of pEGFP-N1 plasmid pre-incubated with 3 μg of R$_4$ or R$_4$(S$_2$Pam$_2$Cys) for 30 mins at 37° C., or with a 3:1 ratio of FUGENE to plasmid DNA for 45 minutes at room temperature. After 2 days, cells were harvested and green fluorescence was determined by flow cytometry (A). Cells were also stained with fluorochrome conjugated anti-murine MHC Class II (IA/E) antibody before analysis by flow cytometry (B). Cells expressing high levels of MHC Class II are considered to be mature (shaded parts of the histogram) whereas those that express low levels are deemed immature (unshaded). The percentage of cells in this category is also indicated within each panel as an average and standard deviation obtained by analysing triplicate samples.

To determine if the $R_4$ or $R_4(S_2Pam_2Cys)$ constructs were capable of inducing expression of transfected DNA, a murine DC line, D1, was transfected with the pEGFP plasmid using $R_4$ or $R_4(S_2Pam_2Cys)$ (FIG. 4A). The expression levels of green fluorescent protein (GFP) in these cells were compared to those levels in D1 cells that were transfected using the commercially available transfection reagent FUGENE.

No fluorescence was observed in untreated cells, cells treated with DNA only and cells treated with $R_4$ together with DNA. However, cells transfected with $R_4(S_2Pam_2Cys)$ and DNA expressed GFP at a level comparable to the level of expression observed in cells transfected with the pEGFP and the FUGENE reagent.

The D1 cell cultures were also found to comprise of two distinct cell populations that were either MHC Class II$^{low}$ or MHC Class II$^{high}$, corresponding to immature and mature cells respectively (FIG. 4B). Approximately 4% of untreated D1 cells were MHC Class II$^{high}$. Treatment with DNA alone or together with R$_4$ did not appreciably alter the expression of MHC Class II on D1 cells. D1 cells treated with DNA and FUGENE comprised approximately 36% MHC Class II$^{high}$ cells, and D1 cells treated with R$_4$(S$_2$Pam$_2$Cys) and DNA comprised approximately 82% MHC Class II$^{high}$ cells.

Figure 5:
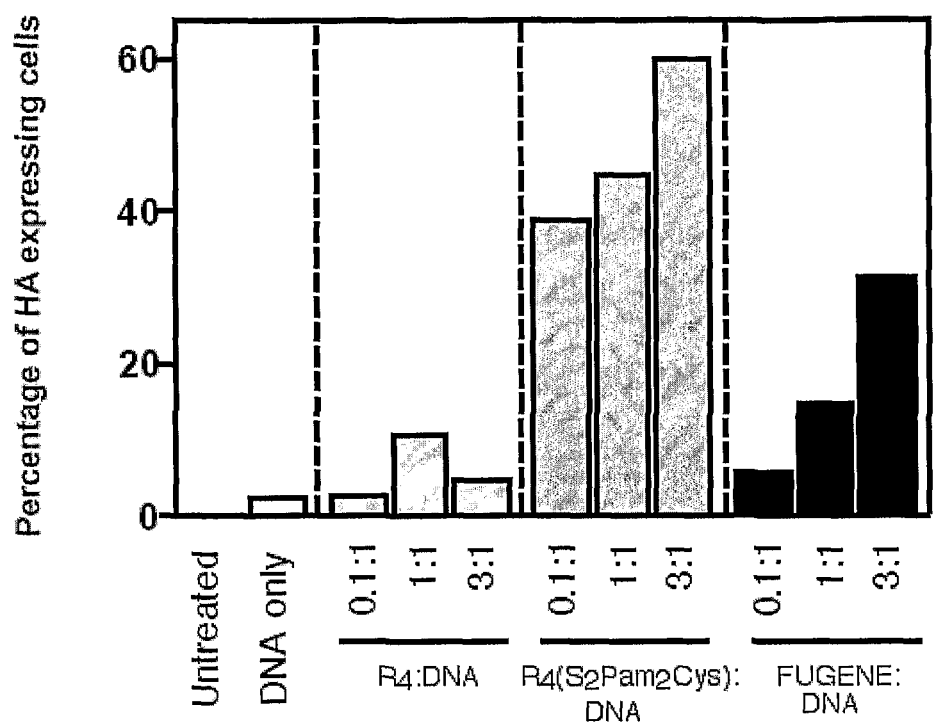
FIG. 5 is a graphical representation of transfection of D1 cells using different ratio mixtures of transfection reagent to DNA. D1 cells (4×10$^5$) derived from BALB/c splenocytes were cultured for 48 hours, at 37° C. in 5% CO$_2$, with 1 μg of pCI-HA plasmid pre-incubated with different ratios of R$_4$ or R$_4$(S$_2$Pam$_2$Cys) for 30 mins at 37° C., or with different ratios of FUGENE for 45 minutes at room temperature. Cells were then harvested and stained with an anti-HA antibody (clone E2.6) that was detected with a FITC-conjugated goat anti-murine 1 g antibody before analysis by flow cytometry.

Transfection efficiency using different ratio mixtures of transfection reagent to DNA was also investigated by incubating D1 cells with increasing amounts (0.1, 1 or 3 µg) of R$_4$, R$_4$(S$_2$Pam$_2$Cys) or FUGENE pre-incubated with a constant amount (1 µg) of pCI-HA plasmid (FIG. 5). Cell surface influenza HA protein expression was determined using a HA-specific antibody. In the case of when R$_4$(S$_2$Pam$_2$Cys) or FUGENE were used, transfection efficiency, as indicated by the percentage of cells expressing surface HA protein, was proportional to the amount of transfection agent used. The exception to this was when R$_4$ was employed. Here, although HA expression levels were lower than those induced by DNA mixtures containing R$_4$(S$_2$Pam$_2$Cys) or FUGENE, transfection appeared to be optimal when there was an equal weight to weight ratio of R$_4$ to DNA. A higher ratio, however, was found to be detrimental to transfection efficiency.

At all of the ratios examined, R$_4$(S$_2$Pam$_2$Cys) was found to be superior to FUGENE at inducing the expression of antigen. The maximum percentage of cells that transfected using R$_4$(S$_2$Pam$_2$Cys) and DNA was 60% at a 3:1 ratio. In comparison, only around 30% of HA positive cells were detected when an equivalent ratio of FUGENE to DNA was used.

Example 5

Transfection of Human Monocyte-Derived Dendritic Cells (MoDCs)

Figure 6:
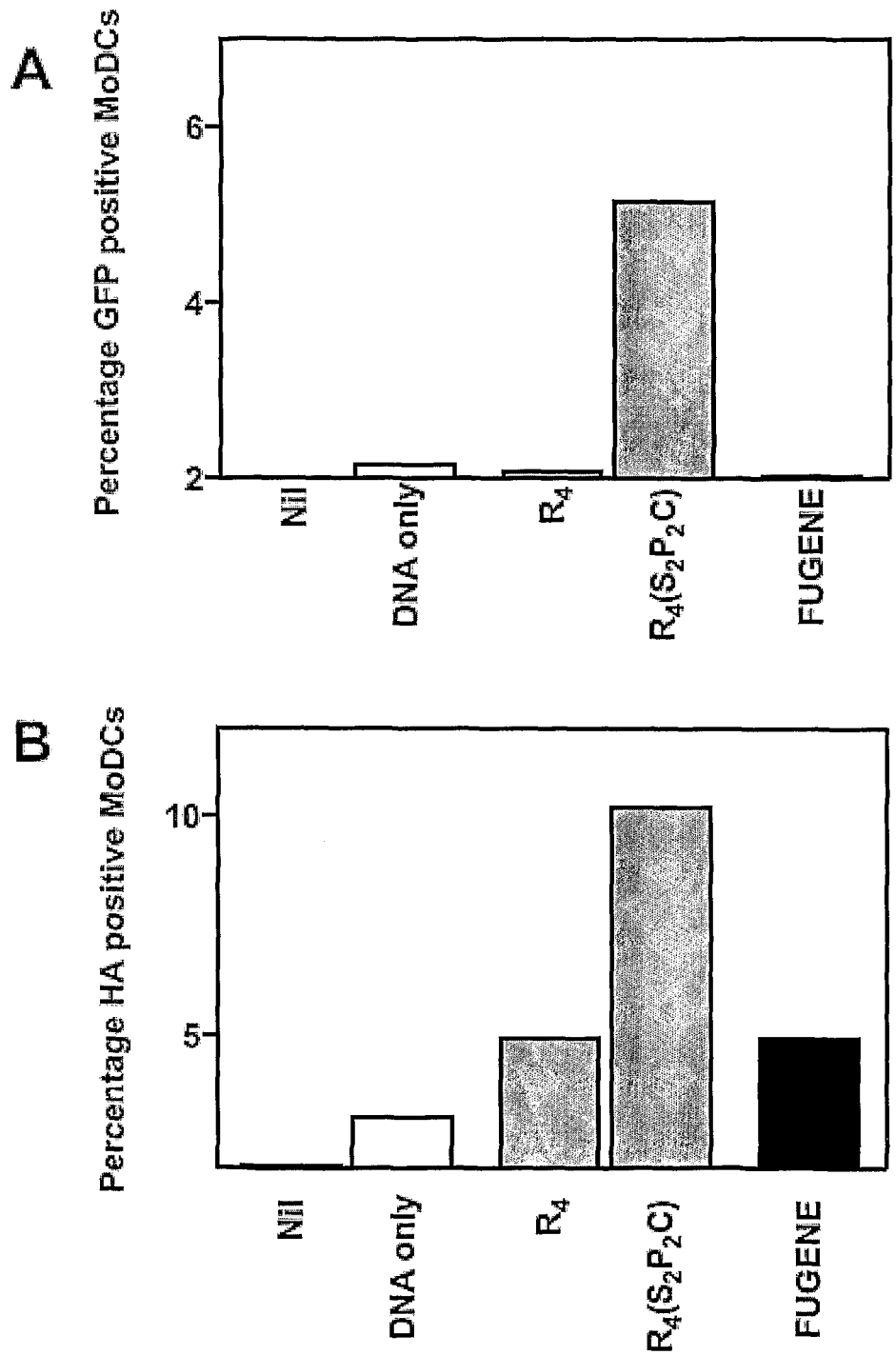
FIG. 6 is a graphical representation of transfection of human, monocyte-derived dendritic cells (MoDCs) with plasmids, pEGFP-N1 and pCI-HA. Monocyte-derived dendritic cells ($2\times10^5$) were cultured at 37° C. in an atmosphere of 5% $CO_2$ with 1 µg of pEGFP-N1 plasmid pre-incubated with 3 µg of $R_4$ or $R_4(S_2Pam_2Cys)$ for 30 mins at 37° C., or with a 3:1 ratio of FUGENE to plasmid DNA for 45 minutes at room temperature. After 2 days, cells were harvested and green fluorescence protein in cells transfected with the pEFGP-N1 plasmid was determined by flow cytometry (A). For cells transfected with the pCI-HA plasmid, a fluorochrome conjugated anti-HA antibody was used to detect the surface expression of HA protein (B).

The ability of R$_4$(S$_2$Pam$_2$Cys) to enhance transfection of human monocyte-derived dendritic cells (MoDCs) was investigated. In an experiment where MoDCs were transfected with the pEGFP plasmid (FIG. 6A), only R$_4$(S$_2$Pam$_2$Cys) was efficient at inducing the expression of GFP. Transfection of cells with pEGFP plus either FUGENE or R$_4$ was relatively inefficient, with the transfection levels in these cells similar to those treated with the plasmid alone. This result was repeated in experiments where MoDCs were transfected with the pCI-HA plasmid together with each of the transfection reagents (FIG. 6B).

Example 6

Transfection of Non-DC Cell Lines with R$_4$(S$_2$Pam$_2$Cys)-DNA

Figure 7:
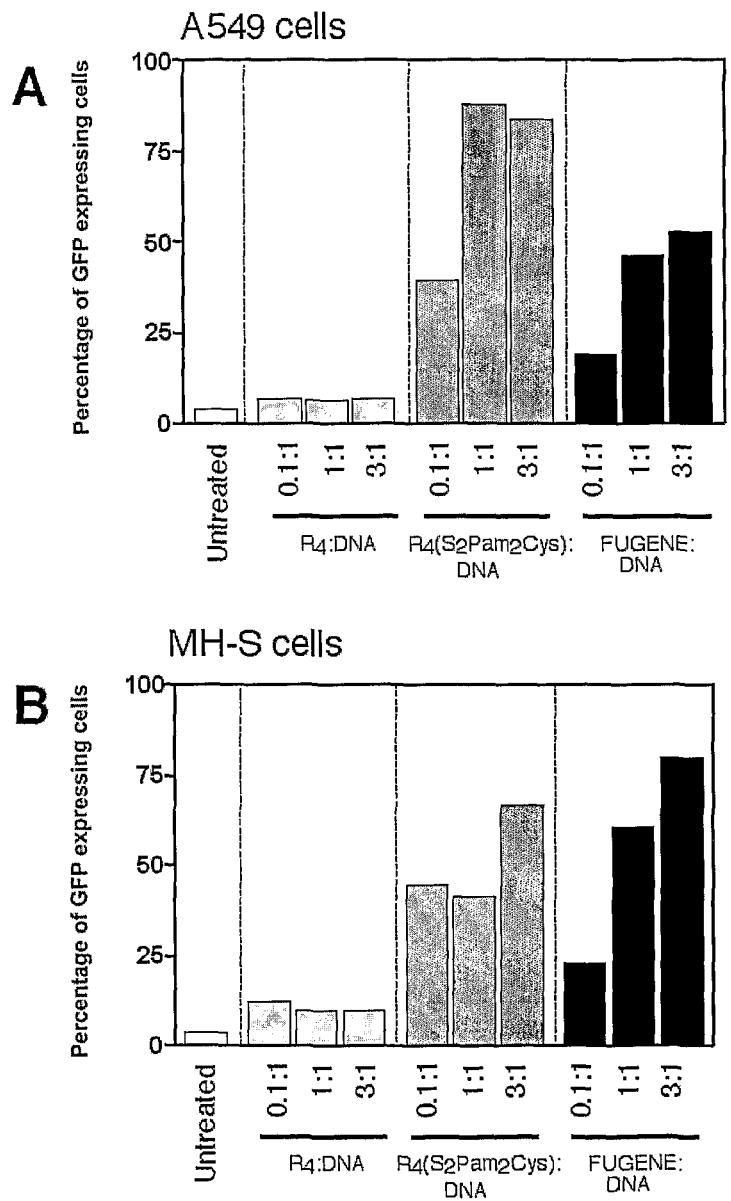
FIG. 7 is a graphical representation of transfection levels of green fluorescent protein in two different cell lines using different ratio mixtures of transfection reagent to DNA. The human lung epithelial cell line A549 (A) or the murine lung aveolar macrophage cell line MH-S (B) were cultured at a concentration of $2\times10^5$ cells/ml in the absence or presence of plasmid encoding for green fluorescent protein complexed with different dilutions of $R_4$, $R_4$ $Pam_2Cys$ or FUGENE for 48 hours at 37° C. and 5% $CO_2$. Transfection efficiency was determined by measuring the fluorescence of cells on a flow cytometer.

To investigate if R$_4$ or R$_4$(S$_2$Pam$_2$Cys) constructs complexed with DNA were capable of transfecting non-DC cell lines, the human lung epithelial cell line A549 and the murine lung aveolar macrophage cell line MH-S were transfected with the pEGFP plasmid using R$_4$ or R$_4$(S$_2$Pam$_2$Cys) (FIGS. 7A and 7B). The human lung epithelial cell line A549 (A) or the murine lung aveolar macrophage cell line MH-S (B) were cultured at a concentration of 2×10$^5$ cells/ml in the absence or presence of plasmid encoding for green fluorescent protein complexed with different dilutions of R$_4$, R$_4$ Pam$_2$Cys or FUGENE for 48 hours at 37° C. and 5% CO$_2$. Transfection efficiency was determined by the measuring the fluorescence of cells on a flow cytometer. Both these cell lines have been reported in other studies to express TLR-2 (Oshikawa 2003, Slevogt 2007). Little to no fluorescence was observed in untreated A549 or MH-S cells and in cells treated with R$_4$ together with DNA. However, A549 or MH-S cells transfected with R$_4$(S$_2$Pam$_2$Cys) and DNA expressed GFP at a level comparable, if not higher, to the level of expression observed in cells transfected with the pEGFP plasmid and the FUGENE reagent.

Example 7

Specific Antibody Production in Mice Immunised with R$_4$(S$_2$Pam$_2$Cys)-DNA

Figure 8:
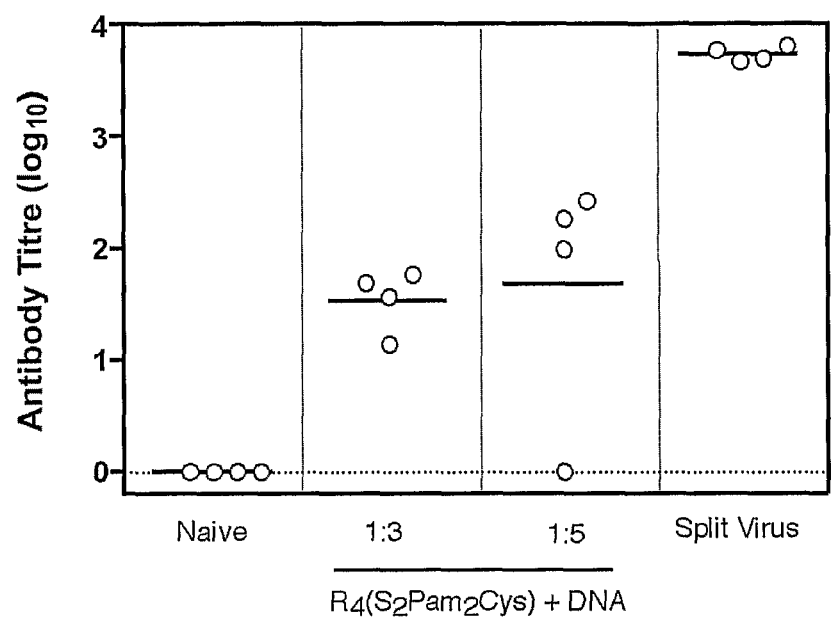
FIG. 8 is a graphical representation of HA-specific antibody levels in unimmunised mice, and mice immunised with either complexes of $R_4$ $Pam_2Cys$ and DNA, or influenza virus. BALB/c mice (6-8 weeks old) were inoculated sub-cutaneously at the base of the tail on day 0 and 28 with 50 µg of DNA plasmid comprising DNA encoding influenza hemagglutinin, either alone or complexed with $R_4(S_2Pam_2Cys)$ at molar ratios of 1:3 or 1:5. As a positive control, mice were also immunised intra-nasally with split PR8 virus (3 µg/mouse). Unimmunised mice served as negative controls. Sera were obtained from mice 14 days after the last inoculation and ELISA was performed to detect the presence of antibodies specific for influenza PR8 virus.

The ability of R$_4$(S$_2$Pam$_2$Cys) complexed with DNA to induce antibodies was assessed. BALB/c mice (6-8 weeks old) were inoculated sub-cutaneously at the base of the tail on day 0 and 28 with 50 µg of DNA plasmid comprising DNA encoding influenza hemagglutinin, either alone or complexed with R$_4$(S$_2$Pam$_2$Cys) at molar ratios of 1:3 or 1:5. As a positive control, mice were also immunised intra-nasally with split PR8 virus (3 µg/mouse). Unimmunised mice served as negative controls. Sera were obtained from mice 14 days after the last inoculation and an ELISA was performed to detect the presence of antibodies specific for influenza PR8 virus. Serum anti-HA antibodies were measured by ELISA. No HA-specific antibodies were detected in unimmunised or "naïve" mice but substantial levels of antibodies that could bind to influenza virus were detected in mice immunised with two doses of R$_4$(S$_2$Pam$_2$Cys) and DNA mixed at molar ratios of 1:3 and 1:5 (FIG. 8).

Example 8

Induction of Influenza Nucleoprotein-Specific, IFN-γ-Positive CD8+ T Cells in Mice Immunised with R$_4$(S$_2$Pam$_2$Cys)-DNA The ability of R$_4$(S$_2$Pam$_2$Cys) complexed with DNA to induce cell-mediated immune responses was assessed. BALB/c mice (6-8 weeks old) were inoculated sub-cutaneously at the base of the tail with 20 µg of DNA plasmid encoding for influenza nucleoprotein either alone or complexed with R$_4$(S$_2$Pam$_2$Cys) at NH$_3^+$: PO$_4^-$ molar ratios of 1:1, 1:2 or 1:5. Complexation was achieved by slowly adding 10 µl aliquots of a solution containing R$_4$(S$_2$Pam$_2$Cys) to a solution of DNA every 2 minutes for a total period of 1 hour. All inoculants were dissolved in 0.7M NaCl. Spleens and inguinal lymph nodes were removed from mice 7 or 10 days after immunizations and intracellular cytokine staining was performed to detect the presence of IFN-γ secreting CD8+ T cells specific for nucleoprotein$_{147-155}$. Each bar represents the mean and standard error from two mice.

Figure 9:
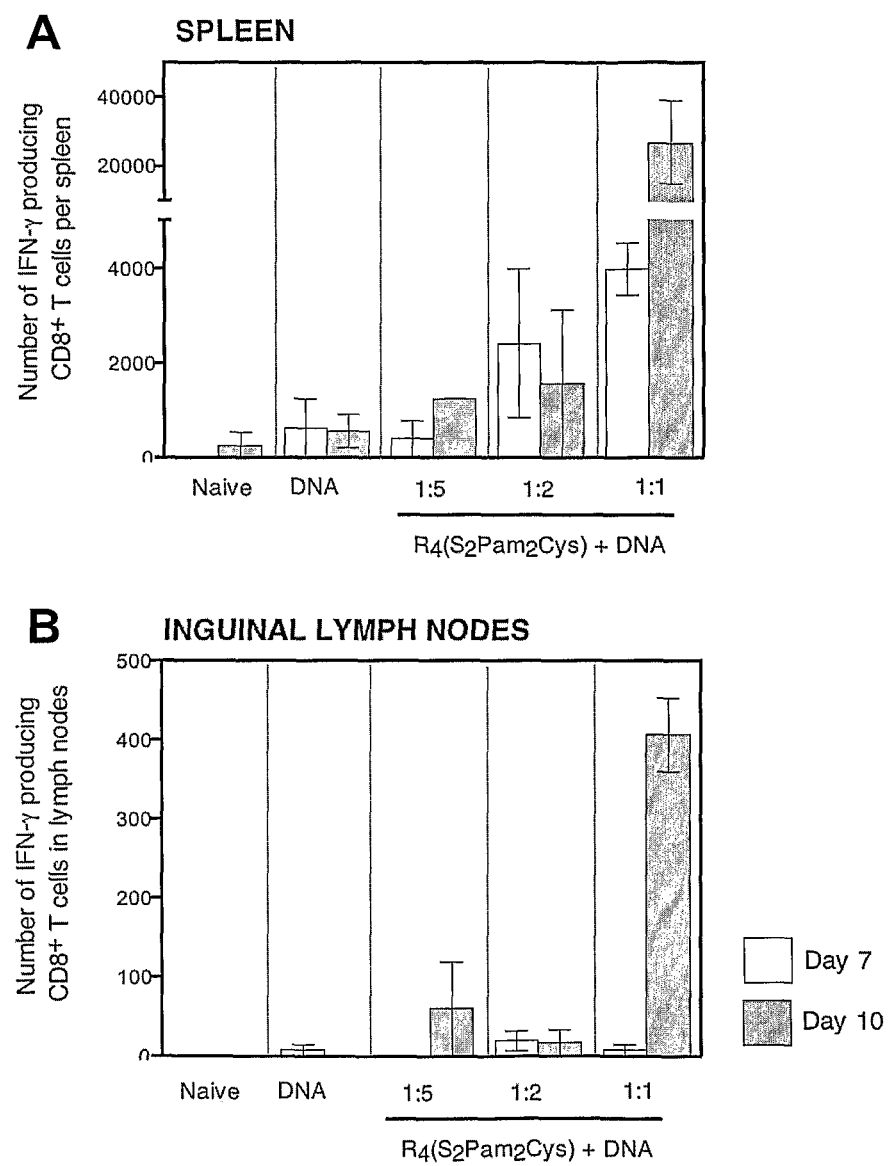
FIG. 9 is a graphical representation of the numbers of antigen-specific, IFN-γ producing CD8+ T cells induced in the spleen (A) and inguinal lymph nodes (B) of mice immunised with complexes of $R_4$ $Pam_2Cys$ and DNA. BALB/c mice (6-8 weeks old) were inoculated sub-cutaneously at the base of the tail with 20 µg of DNA plasmid encoding for influenza nucleoprotein either alone or complexed with $R_4(S_2Pam_2Cys)$ at $NH_3^+$: $PO_4^-$ molar ratios of 1:1, 1:2 or 1:5. Complexation was achieved by slowly adding 10 µl aliquots of a solution containing $R_4(S_2Pam_2Cys)$ to a solution of DNA every 2 minutes for a total period of 1 hour. All inoculants were dissolved in 0.7M NaCl. Spleens and inguinal lymph nodes were removed from mice 7 or 10 days after immunizations and intracellular cytokine staining was performed to detect the presence of IFN-γ secreting CD8+ T cells specific for nucleoprotein$_{147-155}$. Each bar represents the mean and standard error from two mice.

Only very low levels of activated CD8+ T cells were detected in the spleens and inguinal lymph nodes of mice inoculated with DNA alone (FIGS. 9A and 9B respectively) and non were detected in naïve mice. Administration of complexes containing different ratios of R$_4$(S$_2$Pam$_2$Cys) to DNA, however, induced NP-specific IFN-γ producing CD8+ T cells detectable in the spleen 7 days after immunisation (FIG. 9A). Particularly high levels of activated CD8+ T cells were detected in both the lymph nodes and spleens of mice inoculated with a 1:1 ratio of R$_4$(S$_2$Pam$_2$Cys) to DNA (FIGS. 9A and 9B).

BIBLIOGRAPHY

Alexopoulou L., Holt A. C., Medzhitov R. and Flavell R. A. (2001) Recognition of double-stranded RNA and activation of NF-kappaB by Toll-like receptor 3. *Nature* 413 (6857): 732-738

Asea A., Rehli M., Kabingu E., Boch J. A., Bare O., Auron P. E., Stevenson M. A. and Calderwood S. K. (2002) Novel signal transduction pathway utilized by extracellular HSP70: role of toll-like receptor (TLR) 2 and TLR4. *J Biol Chem* 277 (17): 15028-15034

Billingham J., Breen C., Rawson J. O., Yarwood J., Mann B. E. (1997) Adsorption of polycations on clays: A comparative in situ study using $^{133}$Cs and $^{23}$Na solution phase NMR. *Journal of Colloid and Interface Science* 193:183-189

Bulut Y., Faure E., Thomas L., Karahashi H., Michelsen K. S., Equils O., Morrison S. G., Morrison R. P. and Arditi M. (2002) Chlamydial heat shock protein 60 activates macrophages and endothelial cells through Toll-like receptor 4 and MD2 in a MyD88-dependent pathway. *J Immunol* 168 (3): 1435-1440

Buschle M, Schmidt W, Zauner W, Mechtler K, Trska B, Kirlappos H, et al. (1997) Transloading of tumor antigen-derived peptides into antigen-presenting cells. *Proc Natl Acad Sci USA* 94(7):3256-3261

Chow J. C., Young D. W., Golenbock D. T., Christ W. J. and Gusovsky F. (1999) Toll-like receptor-4 mediates lipopolysaccharide-induced signal transduction. *J Biol Chem* 274 (16): 10689-10692

Christiaens B, Grooten J, Reusens M, Joliot A, Goethals M, Vandekerckhove J, Prochiantz A, Rosseneu M. (2004) Membrane interaction and cellular internalization of penetratin peptides. *Eur J Biochem.* 271(6):1187-1197

Fawell S, Seery J, Daikh Y, Moore C, Chen L L, Pepinsky B, et al. (1994) Tat-mediated delivery of heterologous proteins into cells. *Proc Natl Acad Sci USA* 91(2):664-668

Flacher V, Bouschbacher M, Verronèse E, Massacrier C, Sisirak V, Berthier-Vergnes O, de Saint-V is B, Caux C, Dezutter-Dambuyant C, Lebecque S, Valladeau J. (2006) Human Langerhans cells express a specific TLR profile and differentially respond to viruses and Gram-positive bacteria. *J Immunol.* 177(11):7959-7967

Futaki S, Suzuki T, Ohashi W, Yagami T, Tanaka S, Ueda K, et al. (2001) Arginine-rich peptides. An abundant source of membrane-permeable peptides having potential as carriers for intracellular protein delivery. *J Biol Chem* 276(8): 5836-5840

Hayashi F., Smith K. D., Ozinsky A., Hawn T. R., Yi E. C., Goodlett D. R., Eng J. K., Akira S., Underhill D. M. and Aderem A. (2001) The innate immune response to bacterial flagellin is mediated by Toll-like receptor 5. *Nature* 410 (6832): 1099-1103

Heil F., Hemmi H., Hochrein H., Ampenberger F., Kirschning C., Akira S., Lipford G., Wagner H. and Bauer S. (2004) Species-specific recognition of single-stranded RNA via toll-like receptor 7 and 8. *Science* 303 (5663): 1526-1529

Hemmi H., Kaisho T., Takeuchi O., Sato S., Sanjo H., Hoshino K., Horiuchi T., Tomizawa H., Takeda K. and Akira S. (2002) Small anti-viral compounds activate immune cells via the TLR7MyD88-dependent signaling pathway. *Nat Immunol* 3 (2): 196-200

Hemmi H., Takeuchi O., Kawai T., Kaisho T., Sato S., Sanjo H., Matsumoto M., Hoshino K., Wagner H., Takeda K. and Akira S. (2000) A Toll-like receptor recognizes bacterial DNA. *Nature* 408 (6813): 740-745

Husebye H, Halaas Ø, Stenmark H, Tunheim G, Sandanger Ø, Bogen B, Brech A, Latz E, Espevik T. (2006) Endocytic pathways regulate Toll-like receptor 4 signaling and link innate and adaptive immunity. *EMBO J.* 25(4):683-692

Mitchell D J, Kim D T, Steinman L, Fathman C G, Rothbard J B. (2000) Polyarginine enters cells more efficiently than other polycationic homopolymers. *J Pept Res* 56(5):318-325

Morr M., Takeuchi O., Akira S., Simon M. M. and Muhlradt P. F. (2002) Differential recognition of structural details of bacterial lipopeptides by toll-like receptors. *Eur J Immunol* 32 (12): 3337-3347

Oehlke J, Scheller A, Wiesner B, Krause E, Beyermann M, Klauschenz E, et al. (1998) Cellular uptake of an alpha-helical amphipathic model peptide with the potential to deliver polar compounds into the cell interior non-endocytically. *Biochim Biophys Acta* 1414(1-2):127-139

Okusawa T., Fujita M., Nakamura J., Into T., Yasuda M., Yoshimura A., Hara Y., Hasebe A., Golenbock D. T., Morita M., Kuroki Y., Ogawa T. and Shibata K (2004) Relationship between structures and biological activities of mycoplasmal diacylated lipopeptides and their recognition by toll-like receptors 2 and 6. *Infect Immun* 72 (3): 1657-1665

Oshikawa K, Sugiyama Y. (2003) Regulation of toll-like receptor 2 and 4 gene expression in murine alveolar macrophages. *Exp Lung Res* 29(6):401-412

Otvos L., Jr., Cudic M, Chua B Y, Deliyannis G, Jackson D C. (2004) An insect antibacterial peptide-based drug delivery system. *Mol Pharm* 1(3):220-232

Ozinsky A., Underhill D. M., Fontenot J. D., Hajjar A. M., Smith K. D., Wilson C. B., Schroeder L. and Aderem A. (2000) The repertoire for pattern recognition of pathogens by the innate immune system is defined by cooperation between toll-like receptors. *Proc Natl Acad Sci USA* 97 (25): 13766-13771

Pepper M, Dzierszinski F, Wilson E, Tait E, Fang Q, Yarovinsky F, Laufer T M, Roos D, Hunter C A. (2008) Plasmacytoid dendritic cells are activated by *Toxoplasma gondii* to present antigen and produce cytokines. *J Immunol.* 2008 180(9):6229-6236

Poltorak A., He X., Smirnova I., Liu M. Y., Van Huffel C., Du X., Birdwell D., Alejos E., Silva M., Galanos C., Freudenberg M., Ricciardi-Castagnoli P., Layton B. and Beutler B. (1998) Defective LPS signaling in C3H/HeJ and C57BL/10ScCr mice: mutations in Tlr4 gene. *Science* 282 (5396): 2085-2088

Pooga M, Hallbrink M, Zorko M, Langel U. (1998) Cell penetration by transportan. *Faseb J* 12(1):67-77

Schjetne K. W., Thompson K. M., Nilsen N., Flo T. H., Fleckenstein B., Iversen J. G., Espevik T., and Bogen B. (2003) Cutting edge: link between innate and adaptive immunity: Toll-like receptor 2 internalizes antigen for presentation to CD4+ T cells and could be an efficient vaccine target. *J Immunol* 171:32-36

Schwandner R., Dziarski R., Wesche H., Rothe M. and Kirschning C. J. (1999) Peptidoglycan- and lipoteichoic acid-induced cell activation is mediated by toll-like receptor 2. *J Biol Chem* 274 (25): 17406-17409

Slevogt H, Seybold J, Tiwari K N, Hocke A C, Jonatat C, Dietel S, Hippenstiel S, Singer B B, Bachmann S, Suttorp N, Opitz B. (2007) *Moraxella catarrhalis* is internalized in respiratory epithelial cells by a trigger-like mechanism and initiates a TLR2- and partly NOD1-dependent inflammatory immune response. *Cell Microbiol* 9(3):694-707

Takeshita F, Leifer C A, Gursel I, Ishii K J, Takeshita S, Gursel M, Klinman D M. (2001) Cutting edge: Role of Toll-like receptor 9 in CpG DNA-induced activation of human cells. *J Immunol.* 167(7):3555-3558

Takeuchi O., Kaufmann A., Grote K., Kawai T., Hoshino K., Morr M., Muhlradt P. F. and Akira S. (2000) Cutting edge: preferentially the R-stereoisomer of the mycoplasmal lipopeptide macrophage-activating lipopeptide-2 activates immune cells through a toll-like receptor 2- and MyD88-dependent signaling pathway. *J Immunol* 164 (2): 554-557

Takeuchi O., Sato S., Horiuchi T., Hoshino K., Takeda K., Dong Z., Modlin R. L. and Akira S. (2002) Cutting edge: role of Toll-like receptor 1 in mediating immune response to microbial lipoproteins. *J Immunol* 169 (1): 10-14

Wagner E., Zenke M., Cotten M., Beug, H., Birnstiel M. L. (1990) Transferrin-polycation conjugates as carriers for DNA uptake into cells. *Proc. Natl. Acad. Sci. USA* 87:3410-3414

The claims defining the invention are as follows:

1. A positively charged compound comprising a positively charged group linked to at least one TLR-2 or TLR-6 ligand, wherein the positively charged group comprises a branched peptide comprising at least four positively charged amino acid residues, wherein the branched peptide comprises:

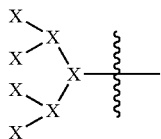

wherein
  each X is independently a lysine residue, an arginine residue or a histidine residue.

2. The compound of claim 1, wherein the TLR-2 or TLR-6 ligand is selected from the group consisting of bacterial lipoproteins, diacylated bacterial lipids, peptidoglycan, yeast zyomosan, $Pam_2Cys$, $Pam_3Cys$, $Ste_2Cys$, $Lau_2Cys$ and $Oct_2Cys$, or wherein the TLR-2 or TLR-6 ligand comprises palmitoyl, myristoyl, stearoyl, lauroyl, octanoyl or decanoyl.

3. A compound according to claim 2, wherein the TLR-2 or TLR-6 ligand comprises palmitoyl, myristoyl, stearoyl, lauroyl, octanoyl, or decanoyl.

4. A compound according to claim 2, wherein the TLR-2 or TLR-6 ligand is selected from the group consisting of: $Pam_2Cys$, $Pam_3Cys$, $Ste_2Cys$, $Lau_2Cys$, and $Oct_2Cys$.

5. A compound according to claim 2, wherein the TLR-2 or TLR-6 ligand is $Pam_2Cys$.

6. A complex comprising a nucleic acid and a compound of claim 1, wherein the nucleic acid is associated with the compound of claim 1 by electrostatic interaction between the nucleic acid and the positively charged group.

7. A complex according to claim 6, wherein the TLR-2 or TLR-6 ligand binds either TLR-2 or TLR-6.

8. A complex according to claim 6, wherein the TLR-2 or TLR-6 ligand comprises palmitoyl, myristoyl, stearoyl, lauroyl, octanoyl, or decanoyl.

9. A complex according to claim 6, wherein the TLR-2 or TLR-6 ligand is selected from the group consisting of: $Pam_2Cys$, $Pam_3Cys$, $Ste_2Cys$, $Lau_2Cys$, and $Oct_2Cys$.

10. A complex according to claim 6, wherein the TLR-2 or TLR-6 ligand binds to TLR-2.

11. A complex according to claim 6, wherein the branched peptide comprises at least four arginine residues or at least four lysine residues.

12. A method of transfection comprising contacting a cell expressing at least one TLR with a complex according to claim 6.

13. A method of raising an immune response against an antigen, comprising administering to a subject a complex according to claim 6, wherein the nucleic acid encodes the antigen or an epitope thereof.

14. A method of raising an immune response against an antigen, comprising administering to a subject cells transfected with a complex according to claim 6, wherein the nucleic acid encodes the antigen or an epitope thereof.

15. A method of repressing expression of a gene in a cell expressing a TLR, comprising administering to a subject a complex according to claim 6, wherein the nucleic acid is selected from the group consisting of: siRNA; shRNA; DNA encoding siRNA; and DNA encoding shRNA, and wherein the siRNA or shRNA is targeted against the gene.

16. A compound according to claim 1 wherein the TLR-2 or TLR-6 ligand binds to TLR-2.

17. A compound according to claim 1 wherein the branched peptide comprises at least one lysine or at least one arginine residue.

18. A compound according to claim 1, wherein the branched peptide is $R_4$, represented by the structure:

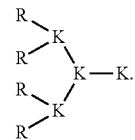

19. A compound according to claim 1, wherein the branched peptide is $K_4$, represented by the structure:

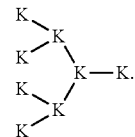

20. A compound according to claim 1, wherein the TLR-2 or TLR-6 ligand is $Pam_2Cys$ and the branched peptide is $R_4$, represented by the structure:

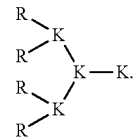

21. A compound according to claim 1, wherein the TLR-2 or TLR-6 ligand is Pam$_2$Cys and the branched peptide is K$_4$, represented by the structure:

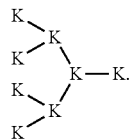

22. A compound of claim 1, wherein the compound is a compound of formula I:

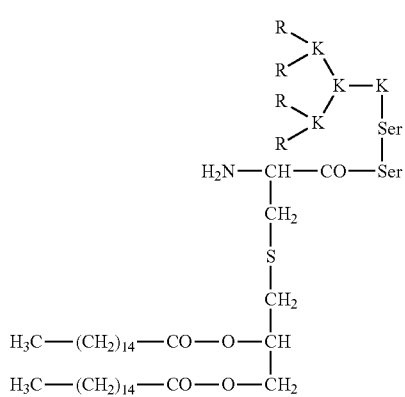

23. compound of claim 1, wherein the compound is a compound of formula II:

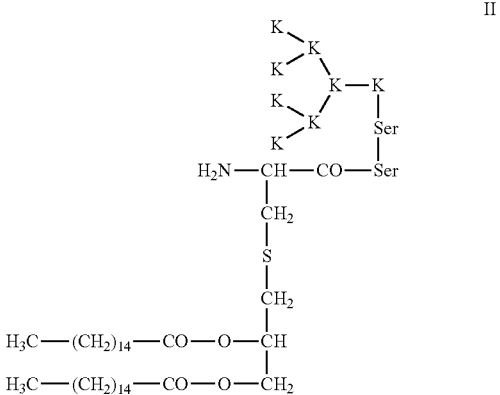

wherein the C-terminal lysine residue is coupled to serine through the epsilon amino group of said C-terminal lysine residue.

* * * * *